(12) United States Patent
Martin

(10) Patent No.: US 7,932,286 B2
(45) Date of Patent: Apr. 26, 2011

(54) METHOD FOR TREATING COLONIC VISCEROSENSITIVITY AND SPASTICITY

(76) Inventor: François Martin, Candiac (CA)

( * ) Notice: Subject to any disclaimer, the term of this patent is extended or adjusted under 35 U.S.C. 154(b) by 175 days.

(21) Appl. No.: 12/183,891

(22) Filed: Jul. 31, 2008

(65) Prior Publication Data

US 2009/0036515 A1 Feb. 5, 2009

Related U.S. Application Data

(60) Provisional application No. 60/952,986, filed on Jul. 31, 2007.

(51) Int. Cl.
*A61K 31/24* (2006.01)
(52) U.S. Cl. ........................................................ 514/535
(58) Field of Classification Search .................. None
See application file for complete search history.

(56) References Cited

U.S. PATENT DOCUMENTS 7,666,907 B2 * 2/2010 Wallace et al. ............... 514/540

OTHER PUBLICATIONS

Delgado-Aros et al., American Journal of Physiology, (2003), 284(4, Pt. 1), G558-G566.*
Oh et al., Clinical Chemistry Acta, (Jan. 2007), 375(1-2):69-75.*
Lupuelle et al., Acta Endoscopica, (May 1997), 27(3), pp. 269-273.*
S. Hoffman et al., "Colonoscopy Without Sedation", J.Clin Gastroenteral 1998: 26(4): 279-282.

* cited by examiner

*Primary Examiner* — Phyllis G. Spivack
(74) *Attorney, Agent, or Firm* — Benoît & Côté

(57) ABSTRACT

There is provided a method of reducing pain associated with colonic viscerosensitivity and spasticity induced during a colonic examination chosen from colonic endoscopy, barium/air contrast colonic radiography and virtual colonoscopy of a non-sedated patient.

17 Claims, No Drawings

METHOD FOR TREATING COLONIC VISCEROSENSITIVITY AND SPASTICITY

FIELD OF THE INVENTION

The present invention relates to a method for treating colonic viscerosensitivity and spasticity. In particular, the invention relates to the use of therapeutic agents for the treatment of certain colonic reactions, which are induced by the procedure of colonic endoscopy, of barium/air contrast colonic radiography and/or virtual colonoscopy. Such reactions can be, for example, specific typical bowel reactions induced by the said procedures such as the painful viscerosensitivity and spasticity induced by aeric, gaseous or liquid distension.

BACKGROUND OF THE INVENTION

Barium/air contrast colonic radiography (Computerised Tomography (CT) colonography) and virtual colonoscopy are radiographic techniques aiming at imaging the colon for anatomical appearance, endoluminal lesions or mucosal abnormalities. In both procedures, a small, flexible tube is passed few inches into the rectum, and a small balloon is inflated to allow air to be gently pumped into the colon using a hand-held squeeze bulb. Sometimes, an electronic pump is used to deliver carbon dioxide gas into the colon. The purpose of the gas is to distend the colon to eliminate any folds or wrinkles that might obscure polyps or other lesions from the physician's view. In the case of colonic radiography, barium (a radio-opaque heavy metal) is also pumped in the rectum, and this barium covers the inner-lining of the colon creating a contrast with the intra-abdominal organs. Mucosal and endoluminal abnormalities can be depicted and diagnostically interpreted by radiologists.

In the case of Virtual colonoscopy, CT colonography uses CT scanning to obtain an interior view of the colon (the large intestine) that is ordinarily only seen with an endoscope inserted into the rectum. CT imaging uses special x-ray equipment to produce multiple images or pictures of the inside of the body and a computer to join them together in cross-sectional views of the area being studied. The images can then be examined on a computer monitor or printed.

Colonoscopy is a test that allows physicians to look at the interior lining of the large intestine (rectum and colon) through a thin, flexible viewing instrument called a colonoscope. A colonoscopy helps detect ulcers, erosions, polyps, tumors, and areas of inflammation or bleeding. During a colonoscopy, tissue samples can be collected (biopsies) and abnormal growths can be removed. Colonoscopy can also be sued as a screening test to identify and remove precancerous and cancerous growths in the colon or rectum.

Before this test, the colon needs to be cleaned out. Colon prep takes 1 to 2 days depending on the preferred prep selected.

Endoscopical or virtual Colonoscopy is usually a painful procedure. Air distension of the colon wall, stretching of the mesenteric attachment and colonic, spastic contractions are usually the causative factors for the pain experienced by the patients. A better tolerability of nociceptive air distension of the colonic wall, and the fewer spastic contractions allow for a reduced time to reach the caecum and successfully complete the colonic examination, for a better patient's tolerance of the procedure, and for a better acceptance of repeated procedures.

No specific guidelines exist to regulate the use of analgesic modalities in the performance of virtual colonoscopy, barium/air contrast colonography or endoscopical colonoscopy.

For endoscopical colonoscopy, it is therefore not surprising to find an impressive list of proposed analgesia and/or sedation modalities that are used in different countries and in different investigation units i.e. hospital-based or out-patient clinic facilities. This list encompasses general anesthesia performed by anesthesiologists, sedo-analgesia performed by anesthesiologists or gastroenterologists, sedo-analgesia performed by a trained nurse. Sedo-analgesia is the most frequently used type of sedation during colonoscopy worldwide. It is usually achieved by combining midazolam with propofol and/or fentanyl or pethidine.

When these proposed pharmacological modalities are administered, a constant patient monitoring during and after the procedure is required to avoid risks of cardio-vascular or respiratory complications, thereby generating increased costs in time, specialized personnel and specialized space allocation. These drawbacks led to the evaluation of the risks and benefits of performing endoscopical colonoscopy with or without sedation. (J. Clin Gastroenterology 1998, June:24(4): 279-282). In summary it is now well accepted that it is feasible and safe to perform a successful colonoscopy without sedation, and this usually does not undermine the willingness of patients to undergo a similar procedure in the future.

It would therefore be highly desirable to be provided with a method that would be an alternative to the previously proposed methods. It would therefore be also highly desirable to be provided with a method that would permit to overcome at least some of the prior art drawbacks.

SUMMARY OF THE INVENTION

In accordance with one aspect of the present invention, there is provided a method of treating colonic viscerosensitivity and spasticity induced by a colonic examination chosen from colonic endoscopy and of barium/air contrast colonic radiography and virtual colonoscopy. The method comprises prescribing and/or administering to a patient in need thereof a pharmaceutically effective oral, sub-lingual, nasal or transdermic dose of a non-centrally-acting opioid agonist for a period of at least two days before the colonic examination.

In accordance with another aspect of the present invention there is provided a method of treating colonic viscerosensitivity and spasticity induced by a colonic examination chosen from colonic endoscopy, barium/air contrast colonic radiography and virtual colonoscopy. The method comprises prescribing and/or administering to a patient in need thereof a pharmaceutically effective intravenous infusion of a non-centrally-acting opioid agonist before carrying out the colonic examination.

In accordance with another aspect of the present invention there is provided a method for carrying out a colonic examination chosen from colonic endoscopy, barium/air contrast colonic radiography and a virtual colonoscopy on a patient comprising:

prescribing and/or administering to the patient a non-centrally-acting opioid agonist to be taken at least once a day for at least two days before carrying out the colonic examination so as to eliminate or reduce the risks of pain generated by colonic viscerosensitivity and spasticity induced during the colonic examination; and introducing into the patient's rectum an endoscope, colonoscope or any instrument required for the colonic examination.

In accordance with another aspect of the present invention there is provided in a method of carrying out a colonic examination chosen from colonic endoscopy, barium/air contrast colonic radiography and a virtual colonoscopy on a patient, the improvement wherein a non-centrally-acting opioid agonist to be taken at least once a day for at least two days before carrying out the colonic examination is prescribed and/or administered to the patient so as to eliminate or reduce the risks of pain generated by colonic viscerosensitivity and spasticity induced during the colonic examination.

In accordance with another aspect of the present invention there is provided a method for eliminating or reducing the risks of pain generated by colonic viscerosensitivity and spasticity induced during a colonic examination. The method comprises administering a non-centrally-acting opioid agonist to be taken at least once a day for at least two days before the colonic examination.

In accordance with another aspect of the present invention there is provided a method of treating colonic viscerosensitivity and spasticity induced by a colonic examination, wherein the elevated threshold for visceral pain, combined with the near abolition of spastic colonic contractions allows for a facilitated progression of an endoscopic instrument or the contrast material requiring less air inflation in the colon.

In accordance with another aspect of the present invention there is provided a method of treating colonic viscerosensitivity and spasticity induced by a colonic examination, wherein the time to reach the patient's caecum is reduced thereby providing the patient's comfort during and after the colonic examination and preparing patient's acceptance for repeated procedure.

In accordance with another aspect of the present invention there is provided the use of a non-centrally-acting opioid agonist for treating viscerosensitivity and spasticity induced during a colonic examination.

In accordance with another aspect of the present invention there is provided the use of a non-centrally-acting opioid agonist for eliminating or reducing the risks of pain generated by viscerosensitivity and spasticity induced during a colonic examination.

In accordance with another aspect of the present invention there is provided the use of a non-centrally-acting opioid agonist in the manufacture of a medicament for eliminating or reducing the risks of pain generated by viscerosensitivity and spasticity induced during a colonic examination.

In accordance with another aspect of the present invention there is provided the use of a non-centrally-acting opioid agonist in a preventive treatment for eliminating or reducing the risks of pain generated by viscerosensitivity and spasticity induced during a colonic examination.

For example, the non-centrally-acting opioid agonist can be chosen from Trimebutine maleate, Nor-desmethyl trimebutine, azimadolin, their salts, isomers or enantiomers, and mixtures thereof.

DETAILED DESCRIPTION OF THE INVENTION

The present invention will be more readily understood by referring to the following example, which represents in a non-limitative manner preferred embodiments.

Example 1

A 52 year old male financial analyst (HB) was referred for colonic polyps screening in the context of familial incidence of colonic cancer; his father had died of metastatic colonic cancer at the age of 62 years. The patient had received a complete colonoscopy three years before in a hospital based gastro-intestinal unit, and this experience left him very anxious concerning the need for a repeat examination. The occurrence of pain during the procedure as well as the discomfort lasting few hours following the colonoscopic examination, despite parenteral sedation/analgesia, was still vivid in his memories. He wanted to negotiate an alternate diagnostic procedure such as a air-contrast barium enema. Because full endoscopical examination of the colon is recognised superior to barium-enema colonography and even to "virtual colonoscopy", he was proposed and finally accepted a new experimental pharmacological preparation consisting in the administration of Trimebutine maleate 200 mg tablets to be taken orally three times a day for three days before the scheduled examination. He was instructed to completed this pharmacological preparation by taking two Fleet® Phospho-soda 45 ml vials with five or six glasses of liquid one in the evening before the examination, and one in the morning two hours before the examination to clean and prepare "clean-rep" the colon. He presented alone to the endoscopy clinic and he was appropriately positioned on his left side on the examination table, and the video-endoscopic colonoscopy was initiated by the endoscopist. The colonoscopy was easily completed to the caecum in 14 minutes. No colonic spastic contractions occurred, and the air-distension of the colon needed for the progression of the instrument did not generate pain or discomfort to the patient. The whole colonic examination including the accurate examination of the colon upon retraction of the instrument lasted a total of 25 minutes and was negative for mucosal lesions and for endoluminal polypoid formations. The patient then dressed up and walked to the endoscopist's office to receive the good results of the examination. He was asked several questions on his experience of the new pharmacological preparation as compared to his previous hospital-based unit experience with parenteral sedation/analgesia. He qualified the experience a very positive one; he said he did not experience any pain and very mild discomfort during the procedure. He admitted to be prepared to receive a repeat procedure with the same preparation in a similar set-up, and was capable to drive home by himself without any assistance or recovery time. The endoscopist and the assistant nurse were very satisfied with the ease and shortness of the completed procedure.

Example 2

A 62 year old female retired nurse (LA) presented with lower, and occasionally generalized, abdominal cramping together with predominantly loose motions. As part of a complete investigation, a colonoscopy was planned. She was prescribed Trimebutine maleate 200 mg tablets to be taken orally three times a day for three days before the scheduled examination. She was instructed to complete the pharmacological preparation by taking two Fleet® Phospho-soda 45 ml vials with five or six glasses of liquid, one in the evening before the examination, and one in the morning two hours before the examination to clean and prepare "clean-prep" the colon. She presented to the endoscopy unit with doubts that she could sustain the planned examination without any other drug preparation, having seen in her career many patients having barely tolerated this procedure of full colonoscopy, even after having received before the examination meperidine and midazolam intravenously. She also remembered the "stress experienced by the endoscopist and the assistant nurse working at completing the examination rapidly and successfully reaching the caecum in these patients". Nonetheless, she consented at trying to receive the examination without further pharmacological preparation, with the promise by the physician that the procedure would be interrupted at her request in the case that she could not tolerate the pain or discomfort. After appropriately positioning the patient on her left side, the instrument was delicately introduced in her rectum, and the progression of the instrument gently initiated. She asked to have her head elevated with a pillow so she could see the video monitor and watch the video-endoscopic recording of her examination. The progression of the instrument in the patient was easy, painless and the caecum was reached in 12 minutes. No spastic contractions delayed the progression of the instrument, and only mild but perfectly tolerable discomfort was experienced by the patient during the examination. The physician and the nurse were surprised by the fact that such a patient presenting a clinical irritable bowel syndrome could experience so little discomfort during the examination since these patients characteristically are chronically suffering from a very low threshold of viscerosentivity with solid or gaseous distension of the colon. After the procedure, she commented that she would accept to repeat the examination any time, and would not hesitate to recommend this pharmacological preparation to patients needing complete colonoscopy, and would be ready to reassure them that there were no more reasons to fear to receive such examination.

Clinical Trial

Patients and Method

A clinical study was then initiated in patients referred by general practitioners to an out-patient endoscopy unit mainly to receive a screening colonoscopy in cases with family history of adeno-carcinoma of the colon. All patients gave informed consent to take part in the trial, which was conducted in accordance with the Revised Declaration of Helsinki.

Exclusion criteria were:
i pregnancy or lactation;
ii significant clinical or laboratory evidence of pulmonary, hepatic or renal disease or dysfunction;
iii need for non-steroidal anti-inflammatory drugs, painkiller drugs or antispasmodic agents.

The study was an open-label, single-institution, unblinded prospective pilot trial aimed at establishing whether a controlled double-blind trial is warranted.

Medication

Trimebutine maleate was used in the form of 200 mg tablets, given three times a day before meals for two or five days before the procedure and for one or two days after the examination Symptom Assessment The severity of symptoms experienced during the examination was assessed by the use of a visual analog scale filled in by the patients only a few minutes after the examination, and a telephone call by the assistant nurse was made two days after the procedure to inquire about any symptom or any event having occurred after the patient had resumed its normal activities. The analog scale consisted of a line marked by numbers at equal intervals from 0 to 10. Zero indicated absence of symptoms while 10 represented symptoms severe enough to interrupt the progression of the endoscopic instrument. Assessed symptoms included abdominal pain/discomfort, abdominal distension and flatulence. Symptom scores were tabulated and statistical were analysis carried out using Students t-test.

This study is in progress and aims at recruiting approximately 50 patients. The results of this study are so far quite encouraging and reflect the results obtained in the individual case studies.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method of reducing pain associated with colonic viscerosensitivity and spasticity induced during a colonic examination chosen from colonic endoscopy and of barium/air contrast colonic radiography and virtual colonoscopy of a non-sedated patient, said method comprising prescribing and/or administering to said patient a pharmaceutically effective oral, sub-lingual, nasal or transdermal dose of a non-centrally-acting opioid agonist chosen from trimebutine maleate and N-desmethyl trimebutine, their isomers, or enantiomers, and mixtures thereof at least once a day for a period of at least two to seven days before said colonic examination, wherein a dosage of said non-centrally-acting opioid agonist is about 300 mg to 1.2 g per day.

2. The method of claim 1, wherein said non-centrally-acting opioid agonist is prescribed or administered at least twice a day for a period of at least three days before said colonic examination.

3. The method of claim 1, wherein a dosage rate administered to said patient commences at a low commencement rate and is escalated over time through at least one larger intermediate rate to a still larger final rate.

4. The method of claim 1, wherein said colonic viscerosensitivity and spasticity is one caused by the procedure of colonic endoscopy or of barium/air contrast colonic radiography or virtual colonoscopy performed for diagnostic or therapeutic purposes.

5. The method of claim 1, further comprising analyzing the results obtained from said colonic examination.

6. The method of claim 1, wherein the dosage rate of said opioid agonist is about 300 mg to 1.2 g per day during at least five days before the colonic examination and during at least two days after the colonic examination.

7. The method of claim 1, wherein the dosage rate of said opioid-agonist is about 300 mg to 1.2 g per day during about five to seven days before the colonic examination and during about two to five days after the colonic examination.

8. The method of claim 1, wherein an elevated threshold for visceral pain, combined with a near abolition of spastic colonic contractions allows for a facilitated progression of an endoscopic instrument or the contrast material requiring less air inflation in the colon.

9. The method of claim 1, wherein the time to reach the patient's caecum is reduced, thereby providing the patient comfort, during and after the colonic examination, and preparing the patient to accept repeated procedures.

10. The method of claim 1, wherein the patient's recuperation after the colonic examination is substantially immediate and avoids postprocedure clinically supervised observation of the patient.

11. The method of claim 1, wherein an anxiolytic and/or analgesic drug is further prescribed or administered orally or sublingually immediately before the colonic examination when the examination is performed in an out-patient clinic or facility with minimum post-procedure clinically supervised observation of the patient.

12. The method of claim 1, wherein an anxiolytic and/or analgesic drug is further prescribed or administered parenterally immediately before the colonic examination when the examination is performed in a hospital-based investigation unit where post-procedure clinically supervised observation of the patient is available.

13. The method of claim 1, wherein said non-centrally-acting opioid agonist is administered by means of a controlled release dosage form.

14. The method of claim 1, wherein said period of at least two to seven days before said colonic examination is three days before said colonic examination.

15. A method of reducing pain associated with colonic viscerosensitivity and spasticity induced during a colonic examination chosen from colonic endoscopy, barium/air contrast colonic radiography and virtual colonoscopy of a non-sedated patient, said method comprising prescribing and/or administering to said patient a pharmaceutically effective intravenous infusion of a non-centrally-acting opioid agonist chosen from trimebutine maleate and N-desmethyl trimebutine, their isomers, or enantiomers, and mixtures thereof at least once a day for a period of at least two to seven days before carrying out the colonic examination, wherein a dosage of said non-centrally-acting opioid agonist is about 300 mg to 1.2 g per day.

16. A method for reducing the pain generated by colonic viscerosensitivity and spasticity induced during a colonic examination of a non-sedated patient, said method comprising administering a non-centrally-acting opioid agonist chosen from trimebutine maleate and N-desmethyl trimebutine, their isomers, or enantiomers, and mixtures thereof to be taken at least once a day for at least two to seven days before the colonic examination, and wherein a dosage of said non-centrally-acting opioid agonist is about 300 mg to 1.2 g per day.

17. The method of claim 16, wherein the opioid agonist is administered by the patient himself or by a health professional.

* * * * *